US011167079B2

(12) United States Patent
MacLaughlan et al.

(10) Patent No.: US 11,167,079 B2
(45) Date of Patent: Nov. 9, 2021

(54) POSITIONABLE DELIVERY DEVICE AND METHOD

(71) Applicant: Profounda, Inc., Orlando, FL (US)

(72) Inventors: Todd Ewen MacLaughlan, Orlando, FL (US); Vinit Gopal Kathardekar, Cupertino, CA (US); Amanullah Abdulhamid Vazir, Chatham, NJ (US)

(73) Assignee: Profounda, Inc., Orlando, FL (US)

( * ) Notice: Subject to any disclaimer, the term of this patent is extended or adjusted under 35 U.S.C. 154(b) by 415 days.

(21) Appl. No.: 15/978,541

(22) Filed: May 14, 2018

(65) Prior Publication Data

US 2018/0256809 A1 Sep. 13, 2018

Related U.S. Application Data

(60) Continuation of application No. 15/223,196, filed on Jul. 29, 2016, now Pat. No. 10,034,974, which is a
(Continued)

(51) Int. Cl.
*A61M 3/02* (2006.01)
*A61M 13/00* (2006.01)
(Continued)

(52) U.S. Cl.
CPC ........... *A61M 3/0279* (2013.01); *A61C 3/025* (2013.01); *A61C 5/62* (2017.02); *A61C 5/66* (2017.02);
(Continued)

(58) Field of Classification Search
CPC .... A61M 3/0279; A61M 13/00; A61M 19/00; A61M 31/00; A61M 2202/04; A61M 2202/064; A61M 2210/0618; A61M 2210/0631; A61M 2210/0662; A61M 2210/0681; A61M 2210/0693; A61M 2210/083; A61M 2210/086; A61M 2210/1067; A61M 2210/1089; A61M 2210/1433; A61M 2210/1475; A61C 5/62; A61C 5/66; A61C 3/025; A61C 17/0202; A61C 19/063; A61C 19/06–19/08; A61C 9/0026; A61C 5/60; A61J 15/00; A61K 9/1629; A61K 31/65; B65D 47/06;
(Continued)

(56) References Cited

U.S. PATENT DOCUMENTS 2,094,966 A 9/1937 Friedman
3,884,231 A 5/1975 Peters
(Continued)

OTHER PUBLICATIONS

EPO Search Report in Corresponding EP14855201.1 dated Aug. 28, 2017.
Preliminary EPO Search Report in corresponding EP14855201.1 dated May 17, 2017.
Patent Examination Report No. 1, dated Oct. 30, 2015 (7 pages) in corresponding Australian Patent Application 2014338565.
(Continued)

*Primary Examiner* — Lauren P Farrar
*Assistant Examiner* — Hamza A Darb
(74) *Attorney, Agent, or Firm* — Irving Fishman

(57) ABSTRACT

A cartridge for delivery of a material therefrom which has a corrugated portion to allow for bending/extending to be applied to the device from which a material to be deposited can be dispensed. The bendability and extendibility allow for greater efficiency in use and application of the material into cavities, pockets, and/or crevices where one needs to deposit the material.

26 Claims, 15 Drawing Sheets

Related U.S. Application Data division of application No. 14/060,159, filed on Oct. 22, 2013, now Pat. No. 9,402,701.

(51) Int. Cl.
| | |
|---|---|
| *A61M 19/00* | (2006.01) |
| *A61M 31/00* | (2006.01) |
| *A61C 5/62* | (2017.01) |
| *A61C 5/66* | (2017.01) |
| *A61C 3/025* | (2006.01) |
| *A61C 17/02* | (2006.01) |
| *A61J 15/00* | (2006.01) |
| *A61K 31/65* | (2006.01) |
| *A61C 19/06* | (2006.01) |
| *A61K 9/16* | (2006.01) |

(52) U.S. Cl.
CPC .......... *A61C 17/0202* (2013.01); *A61C 19/06* (2013.01); *A61C 19/063* (2013.01); *A61J 15/00* (2013.01); *A61K 9/1629* (2013.01); *A61K 31/65* (2013.01); *A61M 13/00* (2013.01); *A61M 19/00* (2013.01); *A61M 31/00* (2013.01); *A61M 2202/04* (2013.01); *A61M 2202/064* (2013.01); *A61M 2210/0618* (2013.01); *A61M 2210/0631* (2013.01); *A61M 2210/0662* (2013.01); *A61M 2210/0681* (2013.01); *A61M 2210/0693* (2013.01); *A61M 2210/083* (2013.01); *A61M 2210/086* (2013.01); *A61M 2210/1067* (2013.01); *A61M 2210/1089* (2013.01); *A61M 2210/1433* (2013.01); *A61M 2210/1475* (2013.01)

(58) Field of Classification Search
CPC ... B65D 25/42; B05C 17/015; B05C 17/0146; B05C 17/01; B05C 17/00503; B05C 17/00533; B05C 17/00
See application file for complete search history.

(56) References Cited

U.S. PATENT DOCUMENTS

| | | | |
|---|---|---|---|
| 4,175,326 A | 11/1979 | Goodson | |
| 4,575,375 A | 3/1986 | Kozam | |
| 4,990,140 A | 2/1991 | Black | |
| 5,000,886 A | 3/1991 | Lawter et al. | |
| 5,004,124 A | 4/1991 | Stefaniak et al. | |
| 5,112,307 A | 5/1992 | Haber et al. | |
| 5,129,825 A | 7/1992 | Discko, Jr. | |
| 5,143,661 A | 9/1992 | Lawter et al. | |
| 5,236,355 A | 8/1993 | Brizzolara et al. | |
| 5,366,733 A | 11/1994 | Brizzolara et al. | |
| 5,500,228 A | 3/1996 | Lawter et al. | |
| 5,622,498 A | 4/1997 | Brizzolara et al. | |
| 5,624,400 A | 4/1997 | Firthe et al. | |
| 5,810,885 A * | 9/1998 | Zinger ............. A61M 25/0021 604/197 |
| 5,947,728 A * | 9/1999 | Riebl ................ B05C 17/00593 433/90 |
| 6,047,864 A | 4/2000 | Winkler | |
| 6,076,712 A | 6/2000 | Esber | |
| 6,083,002 A | 7/2000 | Martin et al. | |
| 6,095,813 A | 8/2000 | Broyles | |
| 6,551,819 B1 * | 4/2003 | Simmet ................ A61D 19/022 222/143 |
| 6,682,348 B2 | 1/2004 | Lawter et al. | |
| 7,699,609 B2 | 4/2010 | Lawter et al. | |
| 2004/0142042 A1 | 8/2004 | Lawter et al. | |
| 2004/0152042 A1* | 8/2004 | Lawter ............. B05C 17/00593 433/90 |
| 2012/0053528 A1 | 1/2012 | Bollenbach et al. | |

OTHER PUBLICATIONS

International Search Report and Written Opinion of the International Search Authority in corresponding PCT/IB2014/067147.
Arestin Product Label 2001 (Picture on p. 10).
OraPharm 2000 Annual Report Picture.
FDA Warning Letter attachment Feb. 2001.

* cited by examiner

POSITIONABLE DELIVERY DEVICE AND METHOD

CROSS-REFERENCE TO RELATED APPLICATIONS

This application is a continuation of pending U.S. Ser. No. 15/223,196, filed Jul. 29, 2016, which is a division of U.S. Ser. No. 14/060,159, filed Oct. 22, 2013, now U.S. Pat. No. 9,402,701, issued Aug. 2, 2016, the priority of each of which is claimed herein.

STATEMENT REGARDING FEDERALLY SPONSORED RESEARCH OR DEVELOPMENT

Not Applicable

FIELD OF THE INVENTION

The present disclosure is directed to a cartridge for delivery of a substance and methods of delivering the same to a cavity.

BACKGROUND OF THE INVENTION

Physicians use a variety of instruments to deliver a medicament to different cavities in a mammalian body. A typical instrument used to deliver a medicament is a syringe with a needle or a cartridge. Needles and cartridges can be made using a metal or a non-metal material. One such example of a mammalian cavity is the cavity between the gums and teeth. Dentists routinely deliver medicaments to this cavity in an effort to treat periodontal disease.

Periodontal disease is a term used to describe dental conditions associated with gingivitis or periodontitis. Gingivitis is an inflammation of the gingiva, commonly known as gums, that is commonly associated with poor oral hygiene and/or the hormonal state of the patient. If left untreated, gingivitis may develop into periodontitis.

Periodontitis is a bacterial disease in which the infection has progressed to involve the oral tissues that retain the teeth in the jawbone. With this disease the gums become red and inflamed. This condition, if untreated, results in damage to the ligaments and bone holding the teeth in place, and formation of pockets around the teeth. As the pockets become deeper, teeth loosen, to a point where they may fall out. The severity of periodontitis is determined by dentists, and other dental practitioners, by measuring the depth of these pockets and reviewing x-rays of the teeth and jawbone.

Periodontal disease involves a different treatment protocol than other oral diseases. While many oral diseases can be treated with proper hygiene, fluoride, pastes, washes and rinses, periodontal disease is often more retractile to treatment. This is because of differences between the oral and periodontal cavities. The bulk of the oral cavity is essentially an aerobic environment, constantly perfused by saliva. In contrast, the periodontal cavity is more anaerobic, and is perfused by plasma filtrate, known as "crevicular fluid". The growth of microorganisms within the periodontal cavity microenvironment may cause periodontal disease. As the disease progresses, the periodontal microenvironment becomes more anaerobic, and the flow of crevicular fluid increases.

Efforts to treat periodontal disease have met with limited degrees of success. This is because the site of the bacterial infections in the periodontal cavity are largely inaccessible to agents present in the oral cavity as well as agents provided to the oral cavity, such as mouthwashes, rinses and the like. Moreover, the increased outflow of crevicular fluid that accompanies periodontal disease inhibits therapeutic agents placed into the oral cavity from entering the pockets.

Oral systemic administration of antibiotics has been shown to be a useful method of controlling subgingival flora. However, because of side effects, such as those of the digestive system and concerns over bacterial resistance, oral systemic administration has had only limited use in treating periodontal disease. Oral systemic therapy also requires frequent dosing, so patient compliance is frequently a problem.

Efforts leave focused on delivering therapeutic agents directly to these pockets, in some cases, in a controlled release formulation. In general, administration of agents directly to the pocket permits higher local drug concentrations that can be achieved by systemic administration while simultaneously avoiding the GI and other potential side effects of the higher oral systemic dosages needed.

U.S. Pat. No. 4,175,326 to Goodson discloses the use of a drag-filled polymer hollow fiber. The disclosed delivery system is tied around a tooth and gently pressed below the margin of the gingiva so that it resides in the periodontal pocket, and can deliver tetracycline for a prolonged period, such as a week or more. U.S. Pat. No. 5,236,355 (Brizzolara et al) describes a tip for delivery of medicament to a periodontal pocket. U.S. Pat. No. 6,682,348 describes an apparatus comprising a tip capable of delivering material to a periodontal pocket. The tip described in this patent is not positionable to a specified retained angle nor extendable, thereby hindering positioning of the tip (frequently requiring twisting of the device, adding, complexity and making it harder to handle by the user) so that the device is less than optimal and is less efficient for the delivery of material to the desired site of action. U.S. Pat. No. 6,083,002 (Martin et al) and U.S. Pat. No. 4,575,375 (Kozam) describe dispensing cartridges for a liquid or semi-liquid compositions. U.S. Pat. No. 5,129,825 (Discko, Jr) describes a dental syringe and dispensing device. U.S. Pat. No. 5,112,307 (Haber et al) discloses a dental syringe having a medication filled capsule. U.S. Pat. No. 5,004,124 (Stefaniak et al) discloses a device for dispensing a fluid substance. U.S. Pat. No. 6,047,864 (Winkler) discloses an actuating device for dispensing a paste like material. U.S. Pat. No. 5,947,728 (Riebl et al) discloses a dental applicator. Each of the foregoing patents and patent applications (as well as any others mentioned in the present application) are incorporated herein in their entirety by reference except to the extent that the discussion in the present application explicitly states matter in contradiction to such reference or requires, implicitly, due to the context of the discussion in the present application, a different understanding. Furthermore, in the case of such conflicting language or construction, the explicit statements in the present application and the constructions impliedly required by the discussion in the present application shall govern over any contrary interpretation or construction in the otherwise incorporated reference.

There is thus a need for an apparatus that provides the flexibility to a user or a clinician to position the tip to efficiently deliver medicament and/or other materials to cavities within a human body. There is further a need for an apparatus that provides the flexibility of the user to position the tip of to efficiently and appropriately deliver substances to cavities, cracks, and crevices that are outside of the realm of medical applications.

BRIEF SUMMARY OF THE INVENTION

The cartridge and methods disclosed herein improve on the contemporary art by providing a dispensing cartridge that can effectively deliver therapeutic agents directly to a body cavity, especially periodontal pockets. The cartridge disclosed herein can be fitted to any syringe. The cartridge provides the flexibility to position the tip at a desired angle either by the user or during the manufacturing process. This is enabled by the corrugated portion incorporated within the cartridge. The corrugated portion is flexible and/or extendible. The extendible option provides the flexibility of positioning a syringe at an optimal distance from the cavity or to extend the reach of the device into difficult to reach areas. In one preferred embodiment, the corrugated portion allows for flexibility (bendability) without the extendibility. In a second embodiment, the corrugated portion allows for extendibility without significant bendability by the user (although allowing bendability in the manufacturing process). In still another preferred embodiment, the corrugated portion allows for both bendability and extendibility in the manufacturing process and/or by the user.

The cartridge further provides for effective delivery of compositions. In some embodiments, the tip (through which the substance contained in the cartridge exits the cartridge to be deposited in the cavity) is deformable, typically from a circular to an oval or flat shape, upon contact with tissue, including tissue within the body cavity, or (in the periodontal application, teeth or other tissues in dental cavities, whereby this flattened tip may allow for better penetration deeply into pockets for quick and direct application of therapeutic agents into the pocket or respective cavity. This is in addition to the "bending" to a particular angle or "extension" or both which may be provided for by the corrugated portion described more fully hereinafter. However, especially in the use in many areas where the tissues or other surfaces against which the tip would need to be pressed to accomplish this deformation of the tip are very delicate and sensitive structures, such pressure and deformation of the tip are not desirable and dispensed with. Although patents such as U.S. Pat. Nos. 6,682,348 and 7,699,609 indicate that a deformable tip is advantageous in the delivery and such feature is an intimate aspect as to those claims, that document does not take into account the sensitivity of the tissues and the desire not to disrupt the already inflamed tissues. Thus, in a preferred embodiment of the present invention, tip deformability and the act of deforming the tip are undesirable and not in use, even though in other embodiments, such tip deformability may be present and in use. In other non-medical embodiments, the deformable tip portion (when the deformable feature is present) can be deformed appropriately by contact with and pressure applied against any surface or edge of the cavity into which the tip is placed. However, the deformable tip feature is purely optional in these contexts as well. In either case, as the cavity opening gets larger, the potential benefit of the "tip deformability" decreases in importance, and ultimately results in not being of any practical value in larger size cavity openings.

The cartridge is configured for receiving a part of an external force applying member, for example (without limitation), a handle with, for example (without limitation), a spring loaded shaft, in a temporarily locking arrangement therewith. When use is desired, the engaging portion of the cartridge snaps or locks into the handle and the spring loaded shaft is moved into contact with a plunger (or other force translating arrangement or means) (located within the cartridge), pushing the plunger, so as to push the material (contained in the interior of the cartridge) out of the tip into the cavity in question (i.e., the periodontal pocket in the periodontal application) into which the tip had been inserted.

Another embodiment of the invention is directed to a method for treating periodontal disease. This method involves providing an apparatus comprising a force applying member adapted for receiving a body portion of the cartridge. The cartridge has a body portion and a tube portion, the tube portion extending from the body portion, and the tube portion ends in a tip (distal from the body portion), that is configured (in some embodiments) for being deformed to at least one geometry different from its initial geometry. There is also a plunger (or other force translating component), at least a portion of the plunger being slidably housed within the tube portion, the plunger configured for contacting a portion of the force applying member. In a preferred embodiment, there is also a quantity of dry particles, at least a portion of the dry particles being within the tip (in other embodiments, the device may contain liquid or semi-liquid or semi-solid formulations of various viscosities). The force applying member and cartridge are then placed into operative communication each other, for example, by a temporary locking engagement. The tip is moved into at least one periodontal pocket and (if desired) is then optionally deformed, for example, to a substantially flattened geometry. Alternatively (especially if a wall of tissue extends from the cavity opening beyond the cavity), the optional deformation of the tip may be accomplished first and then the tip moved into the cavity opening. In either case, tip deformation is only optional and need not be carried out, and in cases where tip deformation is not specifically desired, the tip need not be deformable. The external force applying member can have a portion of it (for example, without limitation, a spring-loaded shaft), moved to contact the plunger (or actuate one of the alternate force translating means), moving the plunger (or alternate force translating means) so as to deliver the composition to the at least one periodontal pocket.

BRIEF DESCRIPTION OF THE DRAWINGS

Attention is now directed to the accompanying drawing figures, where like reference numerals or characters indicate corresponding or like components. In the drawings.

DETAILED DESCRIPTION OF THE DRAWINGS

Figure 1:
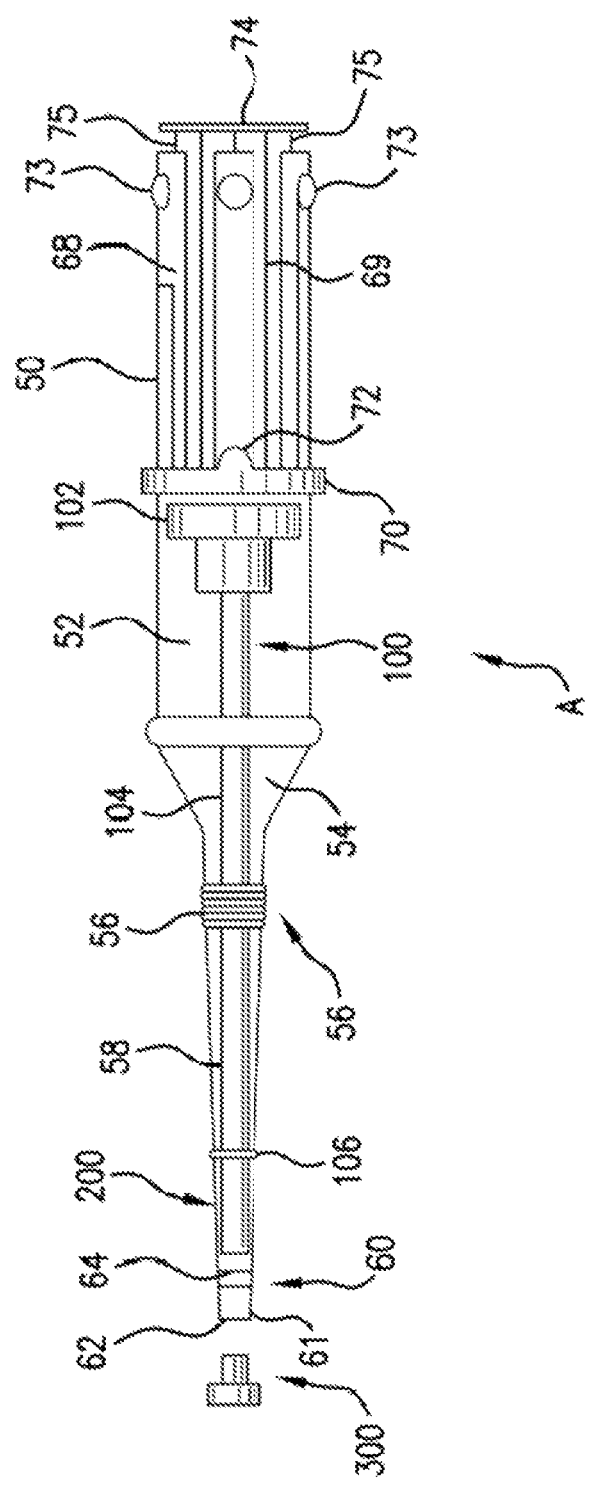
FIG. 1 is a cross-sectional view of a cartridge of the present invention.

FIG. 1 shows a cartridge A, as formed of a body portion 50, an accessible compartment 52, a neck portion 54 connected to a flexible corrugated portion 56. The flexible corrugated portion 56 can be bent or extended as desired. In some embodiments the "bending" into a particular angle or more complicated shape (such an "S" or other bent form) is accomplished during the manufacture. In other embodiments, the desired angle or shape into which the cartridge corrugated portion is bent is accomplished by the user prior to or during use of the cartridge to dispense its contents. The corrugated portion is succeeded by a finger portion 58. The finger portion extends from the corrugated portion 56 and ends in the tip portion 62. The finger portion comprises optional length measure markings 60, which enables the user to determine the length of the finger portion that is inserted in the body cavity/gum pocket/periodontal pocket or any other cavity or opening in question. The length markings (which are optional, but preferred) are on the outside surface of the finger portion 58 extending inwards from the tip portion 62 along the exterior surface of finger portion 58, towards the corrugated portion 56. The tip portion 62 comprises an internal elevated tapering portion 61 along at least some portion of the tip, although the internal elevated tapering portion 61 can run internally along the entire tip portion. The finger portion is further shown in FIG. 1 to comprise an optional dispensable material 200 within the internal walls of the finger portion 58, and generally located in the region between the tip portion 62 and the front end 106 of plunger 100. The cartridge is shown to include an external ridge 64 which is capable of engaging with a cap 300. The cap 300 goes over the tip portion 62 to protect the exposure of the optional dispensable material 200 from being exposed to the external atmosphere. The tip portion 62 in conjunction with the front end 106 of plunger 100 defines an area within the cartridge that can be standardized for use as a measuring volume which is to be filled with the material to be dispensed from the cartridge. In such use of this area as a volume measure, the plunger 100 front end 106 frictionally engages with the interior wall of the finger portion in a manner to seal that region from the remainder of the cartridge and has sufficient friction to resist displacement by the substance 200 filling pressure applied when filling the cartridge therewith through the open tip, but remains slidably engaging such internal wall so as to be capable of moving under applied pressure from the external force applying member (described further below).

FIG. 1 further shows the body portion 50 comprising a generally hollow tubular portion 50A having a radial direction and an axial direction, multiple members 68 extending from the generally hollow tubular portion 50A axially distally away from the accessible compartment 52 of cartridge A. The multiple members 68 are shown (in a first embodiment in FIG. 1) connected to a circular ring 74 located more distally from the hollow tubular portion 50A than the most distal portion of the multiple members 68 is relative to the accessible compartment 52 by means of connectors 75. (For ease of description and convenience (and not limitation), such an arrangement of the position of the circular ring 74 relative to the multiple members 68 may be referred to herein as being "below" the multiple members 68 as when the device is viewed standing vertically with the tip portion 62 at the top) The circular ring 74 is held in place substantially rigidly (preferably rigidly) by vertical rods 69, extending from the generally hollow tubular portion 50A and running parallel to members 68. The multiple members 68 comprise an elevated portion 73 capable of engaging with the external force applying member via a temporary locking mechanism. Also shown is an optional (but preferably present) ring portion 70 with a protrusion 72 which is capable of engaging, with a corresponding dip in the external force applying member as the body portion engages with an external force applying member. In a second embodiment, FIG. 8, connectors 75 are not present so that the ends of the multiple members 68 are free and not fixed in place. In a third embodiment, FIG. 9, ring member 74, connectors 75, and vertical rods 69 are all not present. In yet a fourth embodiment (FIG. 10), body portion 50 is completely replaced by a hollow cylindrical member optionally having elevated portions 73 on the exterior thereof as either one or more discrete elevated portions or a single circular or substantially elevated band, the substantially single circular band being continuous or having one or more cuts there through. It should be noted that the use of the circular ring 74 provides a rigid member for easier use in handling the cartridge and assembling the cartridge to the force applying member and/or handle.

Figure 8:
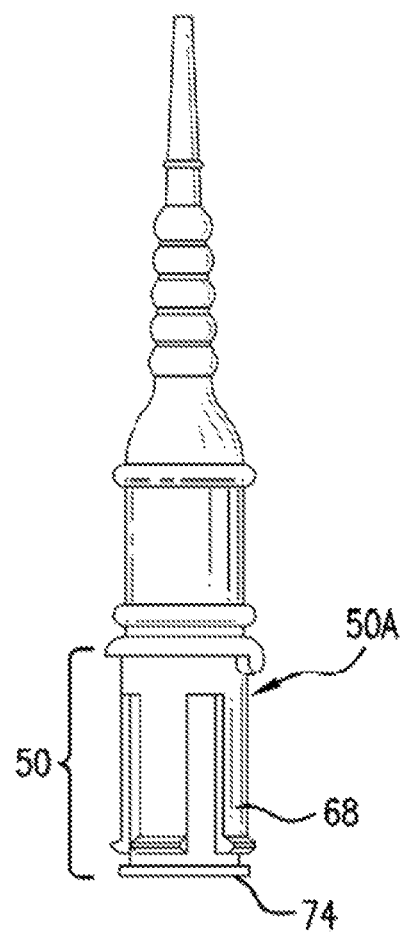
FIG. 8 is similar to FIG. 7 in that it is a magnified view of a second embodiment of the present invention in which connectors 75 are not present in the device of the invention.

As indicating in the preceding paragraph FIG. 8 shows a second embodiment in which connectors 75 are not present so that the ends of the multiple members 68 are free and not fixed in place. In an alternative of this embodiment, rather than multiple members 68 being as free as shown in FIG. 8, one or more multiple members 68 can optionally be attached to another of multiple members 68 on either side by a flexible membrane (not shown in the Figures).

FIG. 1 includes a plunger 100 disposed within the cartridge and extending from the accessible compartment 52 to the finger portion 58. The front end 106 of the plunger 100 is in the proximity of the optional dispensable material 200 and the back end 102 of plunger 100 is disposed within the accessible compartment 52 and are connected by plunger body 104. The plunger 100 is made of flexible material which makes the plunger bendable. The plunger material while bendable cannot be compressed, enabling it to push out the optional dispensable material 200 through the tip 62, as the plunger 100 is pushed forward. The back end or the plunger head 102 of the plunger 100 is capable of engaging with a shaft portion contained within an external force applying member. Alternatives for the plunger 100 include, without limitation, means for translating an externally applied force to the material to be dispensed from the cartridge to force the material from the cartridge into the cavity or pocket into which one intends to dispense it. Such means includes rods, piston, gaseous material, hydraulic fluids, etc., which means are generally known in the art. In the case of gaseous materials and hydraulic fluids, appropriate plugs and/or containers as may be needed to allow the gas or fluid to act appropriately and yet not be introduced into areas where introduction of such gas or fluid would be detrimental to the intended purpose, are also known in the art.

Figure 2:
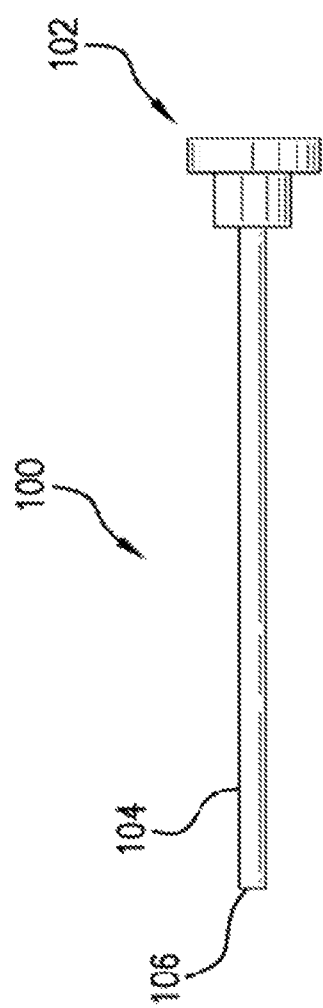
FIG. 2 is one view of a plunger.
Figure 16:
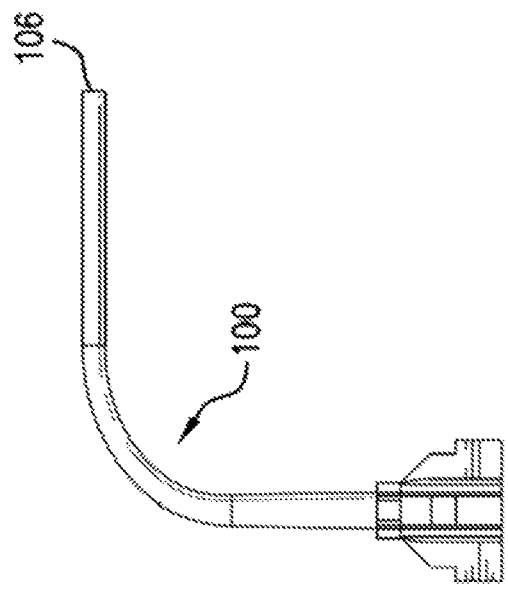
FIG. 16 shows a second exemplary view of a plunger bent in a second angle
Figure 15:
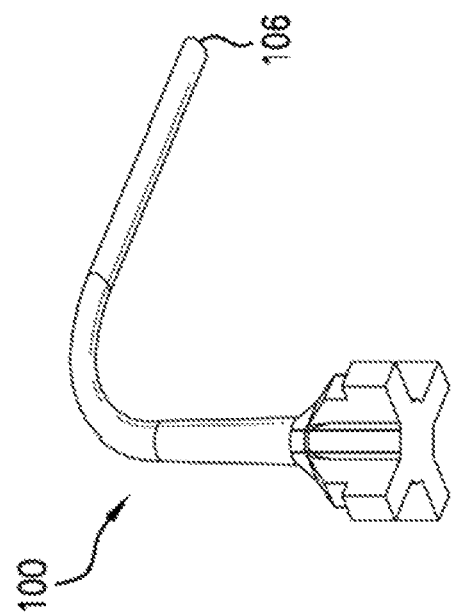
FIG. 15 shows an exemplary view of a plunger bent in a first angle.

FIG. 2 shows the plunger 100 comprising plunger head 102, plunger body 104, and a front end 106. FIGS. 15 and 16 show alternative plungers in two different bent positions. Other angles and complex bendings such as (without limitation) "sigmoidal" shapes are also possible and within the scope of the present invention. The length of the plunger essentially matches the length of the combined length of the accessible compartment 52, the neck portion 54, the extended length of the corrugated portion 56 (required only if extension of the corrugated portion is intended during use), and the finger portion 58. As the plunger is pushed forward by the shaft contained within an external force applying member, the elevated internal tapering portion 61 contained within the tip portion 62 is capable of engaging with the front end 106 of the plunger 100 thereby retarding further forward movement of the plunger and stopping the front end of the plunger from exiting the tip portion 62 of the cartridge. In some embodiments, such as where the plunger 100 is replaced by an alternative external force translating means (as hereinbefore discussed), especially in the embodiments using a gaseous substance or liquid to propel the material 200, a plug (not shown) located between the material 200 to be dispensed and the neck portion 54 is generally used and is of such a size that it effectively separates the gaseous or liquid substance from the area in which the material 200 is located and such plug can slidably move within the finger portion 58 yet (due to internal elevated tapering portion 61) cannot exit the tip portion 62. The forward motion of the plug forces the material 200 out of the tip and into the area intended for material 200 to be deposited. Other alternatives for the plunger 100 work in similar or related manners to either the plunger or the above described gaseous alternative as will be apparent to those of ordinary skill in the art. Plunger 100 can be manufactured in a bent shape or straight as may be convenient for the intended end use. The plunger may be used as a portion of a mold for creating the cartridge interior space so as to have the appropriate construction (straight or bent) of the cartridge corrugation without needing to separately bend the corrugated portion. Such manufacturing and molding techniques will be within the knowledge of those of ordinary skill in the art once having read this specification.

Figure 3:
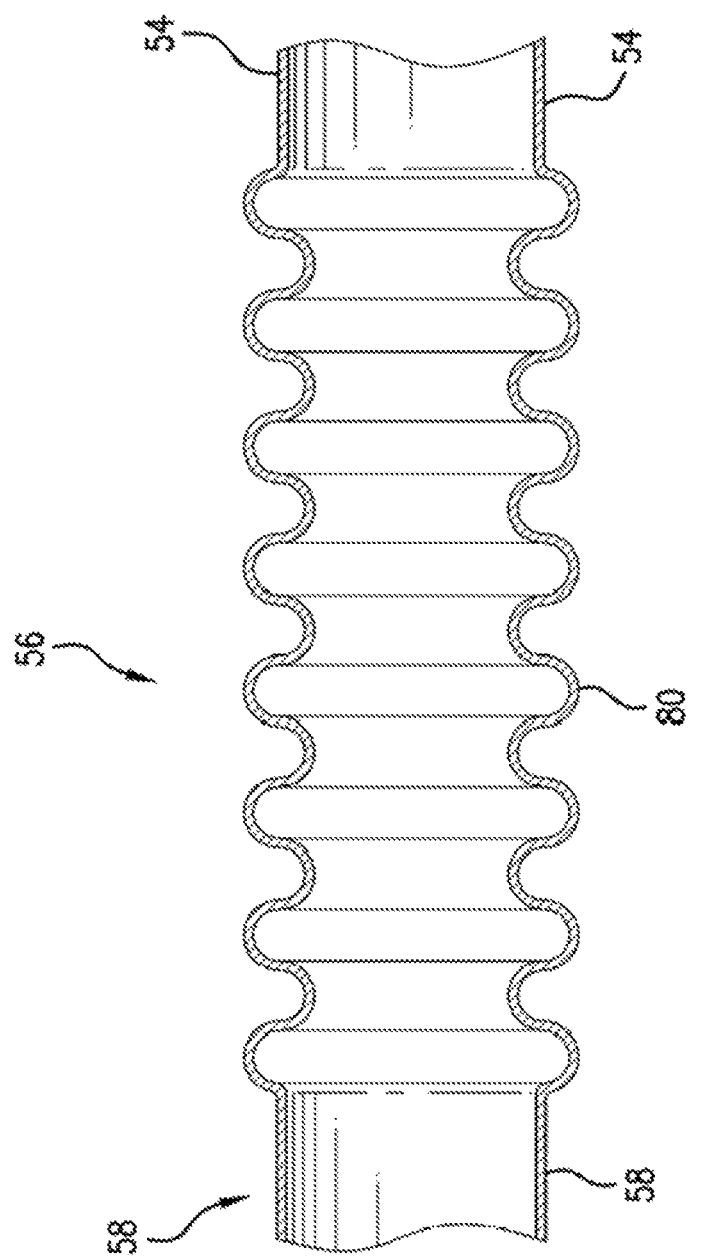
FIG. 3 is a magnified view of a corrugated portion of an embodiment of the present invention.

FIG. 3 depicts a magnified view of one embodiment of the corrugated portion 56 contained within the cartridge A. The magnified view depicts the corrugated portion extended in a straight line (180°) in relation to the finger portion 58 succeeding/following the corrugated portion 56 and the neck portion 54 preceding the corrugated portion 56. The straight extension of the corrugated portion as depicted in this figure enables the user to keep the finger portion in a straight line (180° angle) in relation to the neck portion 54. Also shown in this figure is the elevated portion 80 as part of the corrugated portion 56 as the corrugated portion is extended.

Figure 4:
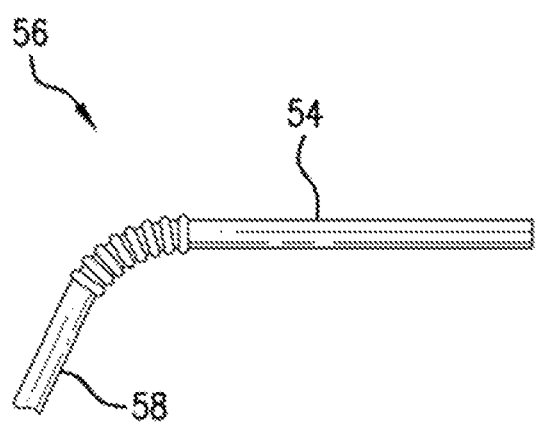
FIG. 4 depicts another magnified view of the corrugated portion of FIG. 3.

FIG. 4 depicts an exemplary (but not limiting) bent view of the corrugated portion 56, as part of the cartridge A. Also shown is a portion of the finger portion 58 succeeding/following the corrugated portion 56 and a portion of the neck portion 54 preceding the corrugated portion 56. The bent view shows the extension of the corrugated portion as depicted in this figure which in turn enables the user to position the finger portion at an angle other than at a 180° angle in relation to the neck portion 54. It is understood that this figure depicts only one of the many possible positions that the corrugated portion can be configured into (whether pre-manufactured as such or manipulated by a user). The corrugated portion 56 can be used to position the finger portion 58 and neck portion 54 at virtually any angle relative to one another, such as, without limitation, about 5°, about 10°, about 15°, about 30°, about 45°, about 60°, about 75°, about 90°, about 105°, about 120°, about 135°, about 150°, about 165°, and about 180° (or any other angle between any two of these) (including complex multiple angles (i.e., contra-angles, for example without limitation, "S" or sigmoidal type arrangements) as long as the plunger 100 has sufficient flexibility to navigate the bend under the externally applied force and actually transmit the force to the material 200. In cases where the plunger cannot effectively transmit the requisite force, one of the alternatives for the plunger that are not similarly impaired by the degree of bend desired, such as, without limitation, those plunger 100 alternatives employing the gaseous or hydraulic means, can be used. In addition, the corrugated portion allows for both a bend and an extension to be applied.

Figure 5:
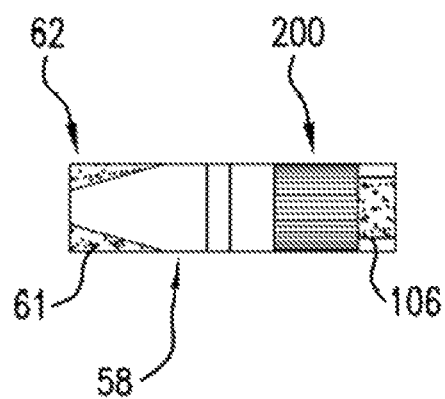
FIG. 5 depicts a magnified view of an embodiment of the finger portion of the present invention.

FIG. 5 depicts a magnified view of the distal portion of the finger portion 58. This figure shows the tip portion 62 comprising an inward tapering portion 61 (which is optional) preceded by the optional dispensable material 200. (In some embodiments, optional dispensing material 200 fills the entire region between the open end of tip portion 62 and the front end 106 of plunger 100; in other embodiments, only a portion of this space is to be filled or is filled with material 200.) As the plunger 100 front end 106 (or plug in those alternatives which utilize a plug) moves forward towards the tip portion 62, it pushes the optional dispensable material out through the opening in the tip portion 62. The inward tapering portion 61 works as a stop thereby preventing the front end 106 of the plunger 100 from exiting the tip portion 61.

Figure 6:
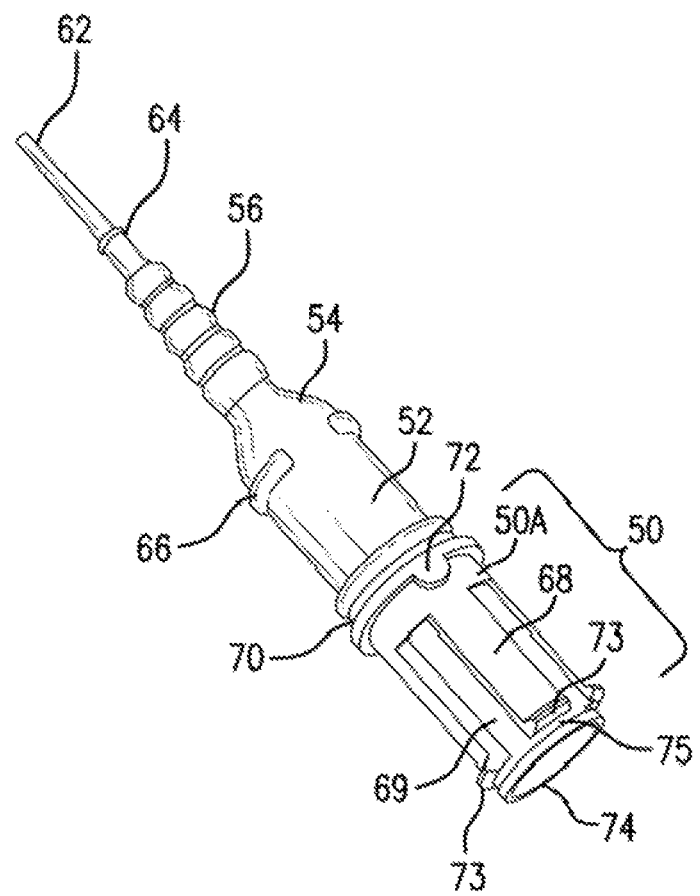
FIG. 6 depicts an outer view of an embodiment of a cartridge of the present invention.

FIG. 6 shows one embodiment of cartridge A, as formed of a body portion 50, an accessible compartment 52, a neck portion 54 connected to a flexible corrugated portion 56. The flexible corrugated portion 56 can be straight, bent, and/or extended as desired (as previously described). The corrugated portion is succeeded by a finger portion 58. The finger portion extends from the corrugated portion and ends in the tip portion 62. The finger portion optionally comprises length measure markings 60 (not shown in FIG. 6, but shown in FIG. 1) which enables the user to determine the length of the finger portion that is inserted in the body cavity/gum pocket/periodontal pocket, and the like. The length markings are on the outside surface of the finger portion 58 extending inwards from the tip portion 62 along the finger portion 58, towards the corrugated portion 56. The cartridge is shown to include an external ridge 64 which is capable of engaging with a cap 300 (not shown in FIG. 6, but shown in FIGS. 1, 14, 17, and 18).

FIG. 6 further shows the body portion 50 comprising a hollow tubular portion 50A having a radial direction and an axial direction, and multiple members 68 extending from the hollow tubular portion 50A along the axial direction thereof distally away from the accessible compartment 52. The multiple members 68 are shown connected to a circular ring 74 located below the multiple members 68 (i.e. even more distally away from the hollow tubular portion 50A than any portion of the multiple members 68) by means of connectors 75. The circular ring 74 (preferably a substantially rigid circular ring, more preferably a rigid ring) is held in place substantially rigidly (preferably rigidly) by vertical rods 69, extending from the hollow tubular portion 50A and running parallel to members 68. The members 68 comprise an elevated portion 73 capable of engaging with the external force applying member via a temporary locking mechanism. Also shown is a ring portion 70 with a (optional) protrusion 72 which is capable of engaging with a corresponding dip in the external force applying member as the body portion engages with the external force applying member.

Figure 7:
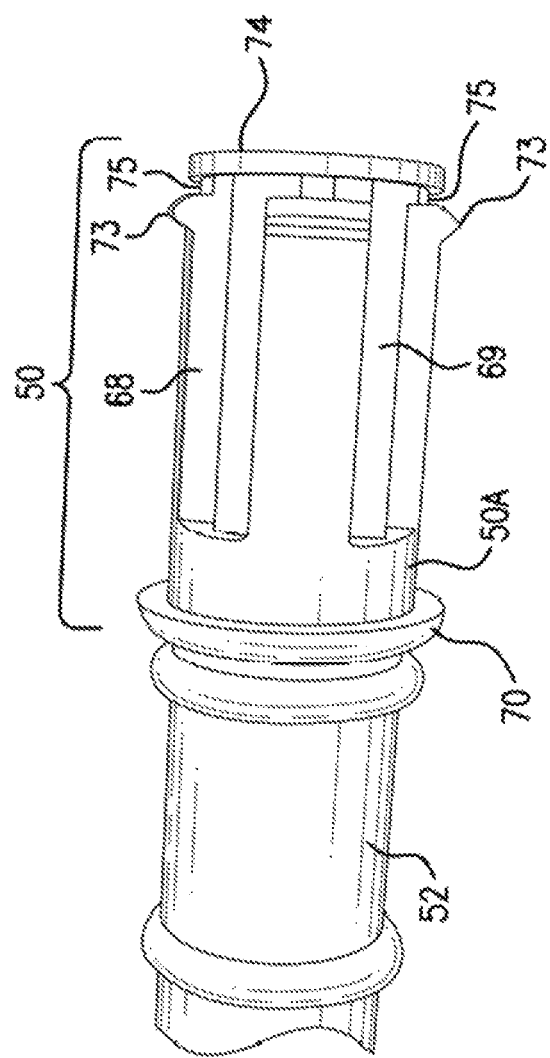
FIG. 7 depicts a magnified view of the body portion of a cartridge of the present invention.

FIG. 7 shows a magnified view of the body portion 50 comprising a hollow tubular portion 50A, multiple members 68 extending from the hollow tubular portion 50A in the axially direction distally away from accessible compartment 52. The multiple members 68 are shown connected to a circular ring 74 located below the multiple members 68 (i.e. even more distally away from the hollow tubular portion 50A than any portion of the multiple members 68) by means of connectors 75. The circular ring 74 is held substantially rigidly (preferably rigidly) in place by vertical rods 69, extending axially from the hollow tubular portion 50A and running parallel to members 68. The members 68 comprise an elevated portion 73 capable of engaging with the external force applying member via a temporary locking mechanism. Also shown is an optional (but preferably present) ring portion 70 which ring portion 70 optionally (but preferably) has a protrusion 72 (not shown in FIG. 7) which is capable of engaging with a corresponding dip in the external force applying member as the body portion engages with an external force applying member.

FIG. 8 is a second embodiment of the cartridge of the present invention. In FIG. 8 the second version of the body portion 50 is shown in greater detail analogous to that shown in FIG. 7, wherein there are no connectors 75 connecting the multiple members 68 to circular ring 74. In this embodiment, the multiple members 68 have a greater degree of freedom than the multiple members 68 have in the embodiment shown in FIG. 7.

Figure 9:
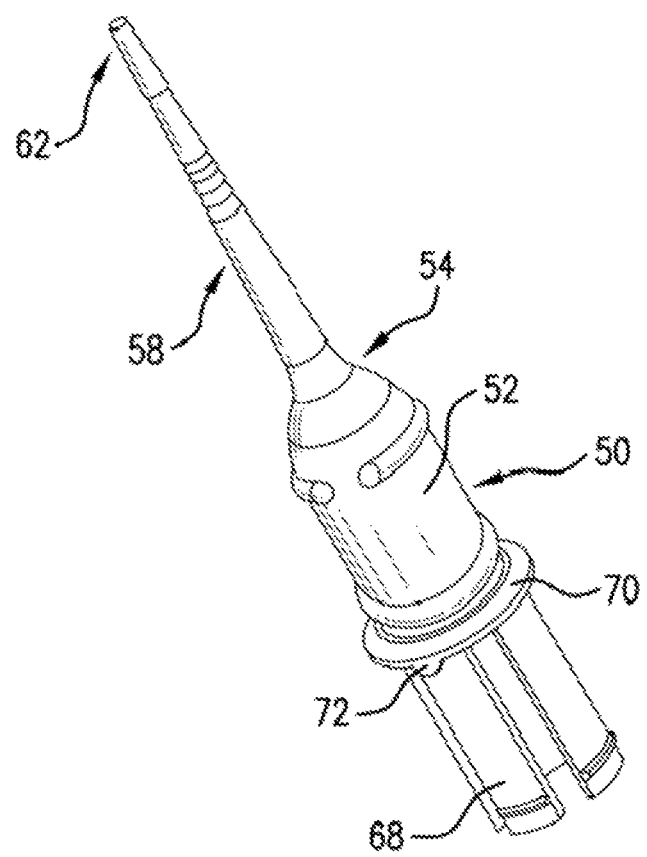
FIG. 9 is also similar to FIG. 7 in that it is a magnified view of a third embodiment of the present invention in which connectors 75, ring member 74, and vertical rods 69 are not present in the device of the invention.

FIG. 9 is a third embodiment of the cartridge of the present invention. In FIG. 9, the third embodiment of the body portion 50 is shown in greater detail analogous to that shown in FIG. 7, wherein there are no connectors 75, no circular ring 74, and no vertical members 69.

Figure 10:
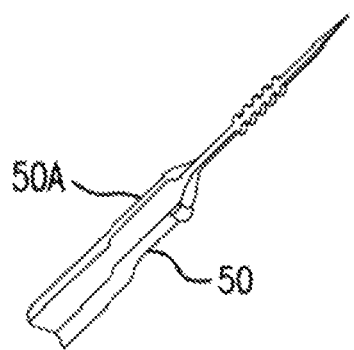
FIG. 10 (shown as a cutaway view) is similar to FIG. 9 in that it is a magnified view of a fourth embodiment of the present invention in which multiple members 68 are also not present and the hollow tubular portion 50A is extended as compared to the device shown in FIG. 9.

FIG. 10 is a fourth embodiment of the cartridge of the present invention. In FIG. 10 the fourth embodiment of the body portion 50 is shown analogous to that shown in FIG. 9, wherein in addition, there are no multiple members 68 and the hollow tubular portion 50A is extended distally away from the tip portion. FIG. 10 is shown partially cut away in the regions of body portion 50 and generally hollow tubular portion 50A to more clearly show the hollow aspect.

Figure 11:
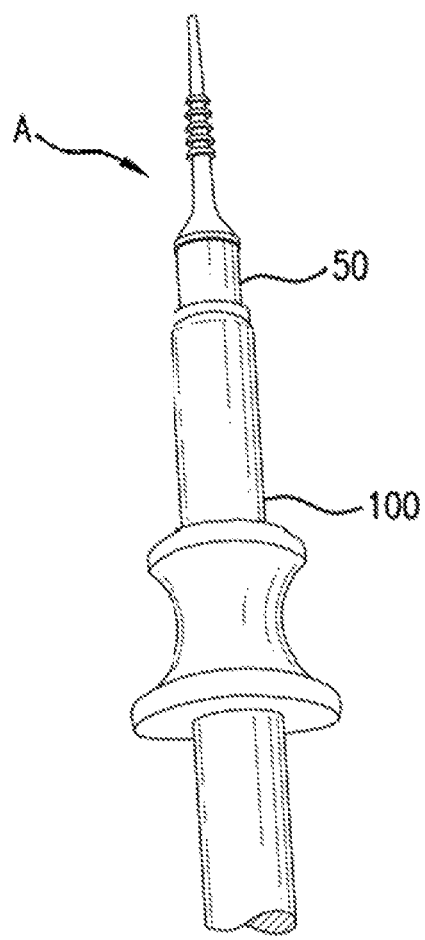
FIG. 11 shows one embodiment of the present invention cartridge assembled with one version of an external force applying member (in this case in particular, a syringe, the syringe being shown only partially).
Figure 12:
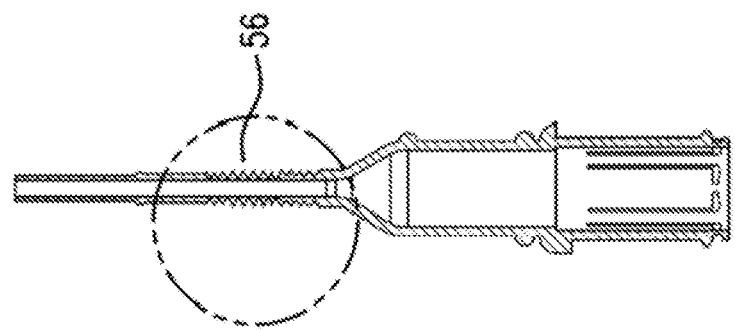
FIG. 12 shows an alternate embodiment of the cartridge of FIG. 1 in which the corrugation shown in FIGS. 3 and 4 does not extend to the inside wall of the device.
Figure 13:
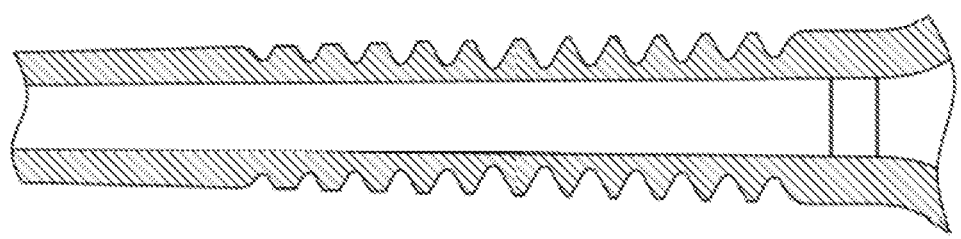
FIG. 13 shows an enlarged view of the corrugated portion of FIG. 12.

FIG. 11 shows one embodiment of the invention cartridge assembled to one embodiment of the external force applying member, in this figure in particular, a syringe, with the syringe only partially shown FIGS. 12 and 13 show an alternate embodiment of the corrugated portion 56. FIG. 13 is a magnified view of the circled portion of FIG. 12. In this embodiment, the corrugations do not extend to the inside wall of the finger portion 58. This allows for better manufacturing as the tools for creating a smooth internal surface in this region are considerably easier to make than the tools needed for creating the corrugation internal surface. In addition, this provides for greater ease of movement of the plunger 100 or alternative therefor in translating the externally applied force to expel the material 200 from the tip portion 62.

Figure 14:
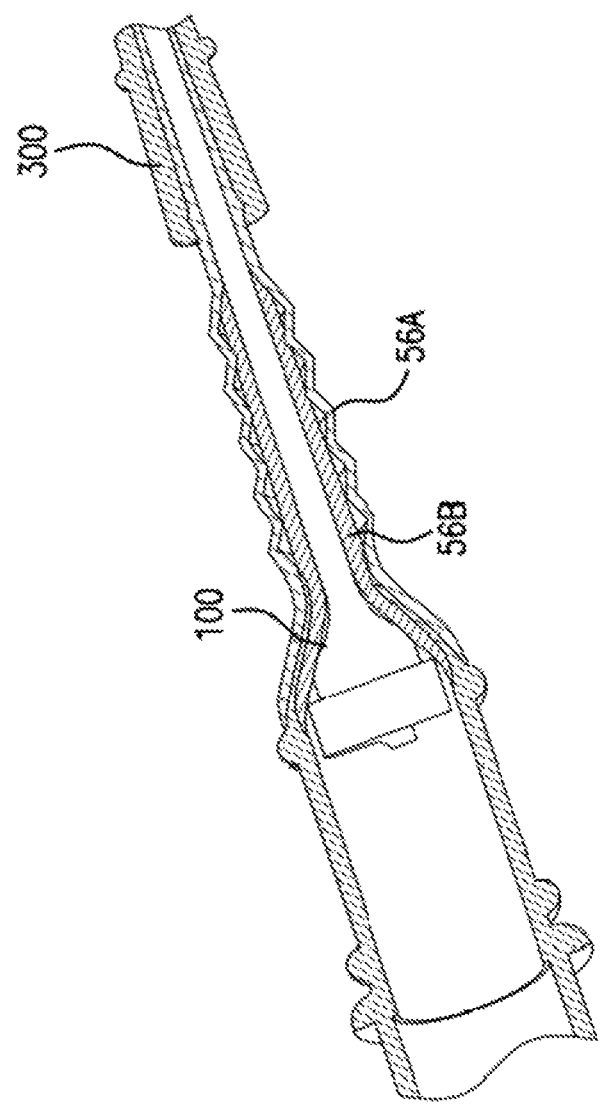
FIG. 14 shows an alternate version of the corrugated region wherein, although the corrugation extends to the inner wall of the hollow cartridge in the corrugated region, the device has an internal sleeve separating the corrugation internal surface from the plunger surface.

FIG. 14 shows a third alternate embodiment in which the corrugated portion 56 contains within it a sleeve 56B which allows for additional variability in the cartridge A manufacture and use. The sleeve 56B provides the smooth internal wall for contacting the plunger while at the same time allows for easier manufacture of the finger portion 58 with the corrugations as compared to the other embodiments where the corrugations of corrugated portion 56 are in contact with the plunger 100. FIG. 14 also shows an alternative cap 300 as compared to that shown in FIG. 1.

FIGS. 15 and 16 show two exemplary (non-limiting) bends in plungers 100 that are manufactured with the bends in place.

Figure 18:
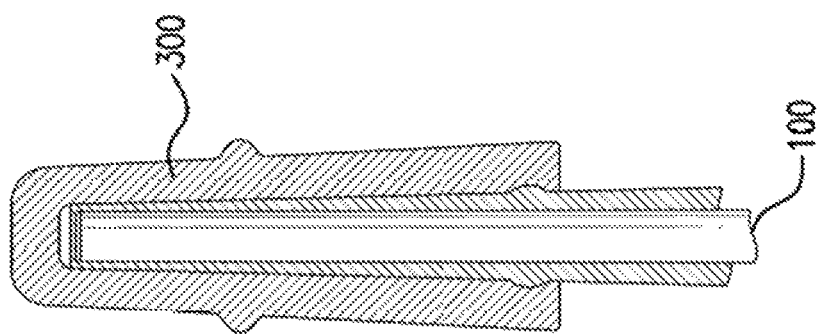
FIG. 18 shows and enlarged view of the cap shown in FIG. 17.
Figure 17:
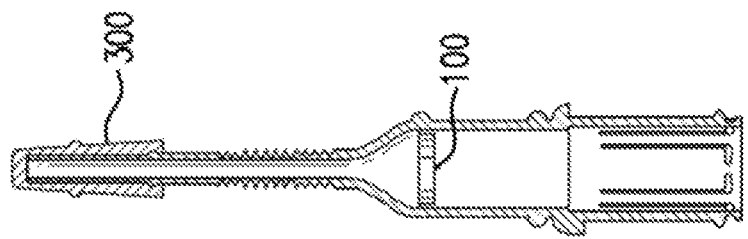
FIG. 17 shows a cartridge of the invention with an alternate cap.

FIGS. 17 and 18 more fully show the cap 300 that is partially shown in FIG. 14.

In each of the foregoing embodiments, where desired, the corrugated portion 56 may have an outer sleeve (not shown in FIGS. 1-18) where it is deemed that the corrugations of corrugated portion 56 outer surface may be irritating or otherwise detrimental to the act of administering the substance 200.

DETAILED DESCRIPTION OF THE INVENTION

The following detailed description will be discussed initially with respect to applications in which material is being dispensed to cavities/crevices, folds, etc. in connection with a mammalian (preferably human) body. However, the description is equally applicable to other animal (non-mammalian) bodies. Furthermore, the invention is also equally applicable to dispensing materials into cavities, crevices, openings that are not connected with animal bodies and include, without limitation, introduction of material into cracks, crevices, and spaces that have limited openings for introduction of materials thereto. The particular uses are limited only by the materials which are to be dispensed by the present invention cartridges.

As seen from the foregoing, the instantly claimed cartridge provides its user a greater range of flexibility in the application of a medicament to a body cavity (in particular the periodontal or gingival pocket). Other body cavities to which the present invention cartridge can be used for delivery of medicament to include, without limitation, the aural cavity, the nasal cavity, the sinus cavities, the rectum, the bladder, the vaginal cavity, the uterus, the navel, surgical openings (to reach internal body parts not otherwise accessible to local administration of medicaments as for example without limitation, internal organs such as the gall bladder, the appendix, the kidney, the heart, the brain, the spinal column, and many others known in the art), surgically created cavities, cavities resulting from disease processes, wounds, etc. Additionally, the present invention cartridge is also suitably used for the deposition of material (preferably medicaments) various cracks and crevices such as, without limitation, the margins around fingernails and toenails, etc., notwithstanding that such "cracks and crevices are not strictly speaking "cavities", but for the purposes of the present invention are preferably to be so considered. The medicament can be placed more precisely and with greater comfort than prior devices due to the ability to the flexible corrugated portion (as in element 56 of the various Figures) in that the length of the finger portion can be extended and/or arranged in a special bent position as desired by the user.

The instantly claimed cartridge (with proper scaling in size for larger or smaller body cavities and dosage amounts to be administered (which will be apparent to those of ordinary skill in the art) can be used to deliver a substance to, for example, any body cavity such as a nasal cavity, periodontal cavity, area around finger and toe nails, ear canal, or the like. Without departing from the scope of the invention, the instantly claimed cartridge can be used for administering substances to human and non-human animals. Further, without departing from the invention, instead of medicament, the instant invention can be used to apply irrigation fluids in otherwise difficult to reach body cavities. In addition, the instant invention cartridge can further be used totally outside the scope of delivery of a medicament to a living being and may be used to deliver material to areas other than a body cavity, such as in construction related uses and the like. Other such non-limiting uses include application of herbicides, fungicides, and/or pesticides to areas where it is difficult to apply material without also applying such material to unintended areas; application of sealants and glues into cavities or crevices or recessed openings; and other analogous uses which will be apparent to those of ordinary skill in the art after becoming familiar with the present disclosure.

The tip portion (exemplified by element 62 of the Figures) which is contained within the finger portion (exemplified by element 58 of the Figures) may comprises malleable material, thereby making the tip portion deformable. Thus for example, the tip portion in such embodiments can be capable of changes in its geometry especially when placed in contact with a surface of the cavity being treated or a surface which leads to the opening of the cavity being treated. (However, such "deformability is merely optional and in practice, pressing the device against the tissues being treated is generally not desirable as those structures are already compromised and sensitive.) In the context of a periodontal pocket, that surface is either a wall of the periodontal pocket or a portion of the tooth or gum outside of the pocket against which the tip portion is pressed allowing for deformation of the opening at the end of the tip portion for potentially better insertion of the tip portion into the cavity being treated. It should be noted that the general tip portion and the opening of the tip portion do not need to be the same type or degree of deformation, and the present invention includes embodiments in which only the tip opening is deformed without deformation of the general tip portion, only the general tip portion is deformed without deforming the tip opening, and deformations of both the tip opening and deformation of the general tip portion. Similarly, the deformation of the tip opening or the remainder of the tip portion is independent of the bend applied or not applied to the corrugated portion 56. Again, although potentially useful in some embodiments to have a deformable tip, such is generally not desired and the preferred embodiment is not to have the tip be deformed in the manner described in this paragraph.

In uses that do not require the use of a plunger, the material contained within the finger portion can be moved forward by other pressure delivery means such as air (or other gas) pressure, or hydraulic pressure (in each case with suitable separation means for keeping the pressure delivery means (other than the separation means) from directly contacting the material for delivery if such pressure delivery means should not contact the material for delivery. The separation means may be in the form of an inflatable or expandable bladder or a slidable non-inflatable plug of sufficient durability that it will not break under the pressure load provided.

The instantly claimed cartridge comprises a body portion which can be modified to engage with a container containing solid, liquid, semi-solid, semi-liquid, moist paste, fluids and the like. In some embodiments, no further impediment is needed to keep the material from exiting the tip portion between the time of cap removal and tip placement into the cavity opening. In other embodiments, in order to keep the material for delivery from exiting the device between the cap removal from the tip and the insertion of the tip into the periodontal pocket (or other delivery point in other applications), a thin membrane may be applied to cover the tip which may be punctured in the course of cap removal and then when the forwardly moving externally applied pressure is actually applied, the membrane rips open more fully to allow dispensing of the material. In an alternative embodiment, the covering membrane is sufficiently thin that on the deformation of the tip portion (when that feature is used), the membrane splits even without being broken in the act of cap removal or the application of the forwardly applied pressure so that upon application of the forward applied pressure, the membrane either splits further or the opening thus made by the deformation of the tip opens sufficiently for delivery of the material contained within the cartridge. In still other embodiments, such as those having a membrane covering the tip portion, the membrane breaks open on application of just the forwardly moving externally applied pressure. In some embodiments, more than one of these actions can be at play in the same device. However, in a preferred and simpler embodiment, there is no membrane preventing the flow of material from the cartridge once the cap is removed. In such cases, the cartridge is engaged with the forward pressure applying means and locked into place thereon. The corrugated portion is arranged as desired, and the engaged cartridge is held in a position that gravitational forces do not cause the material to prematurely exit the tip on removal of the cap. In some embodiments, the material 200 is a formulation of the active agent being applied which is sufficiently cohesive that it does not exit the tip 62 unless the externally applied force is actually applied to the material 200. The cap is then removed while maintaining the cartridge orientation so as to prevent the gravitational forces from causing the exit of material prematurely (if needed). (In cases where the material to be dispensed is either of sufficient viscosity or particles are sufficiently tacky that gravitational forces will not cause the material to exit the tip without the application of the externally applied force, no precaution about holding the device in any particular orientation after the cap is removed is needed.) The tip is then moved to the periodontal pocket opening (or other opening of other cavity in which the material is to be deposited) and any tip deformation pressure (which may or may not be desired) is applied. The cartridge can then be maintained in this orientation while delivery is effected by the application of the forward moving pressure or the cartridge can be moved to an orientation such that gravitational flow of the material will cooperate with the forwardly applied pressure to deliver the material from the cartridge into the periodontal pocket or other cavity to which the material is to be delivered. In yet other alternatives, the material for delivery from the cartridge may be contained within a thin container having a selectively breakable wall under the action of one or more of the above described methods of breaking and further opening the described membrane. The selectively breakable wall of the container is oriented toward the tip opening so that upon breakage of the selectively breakable wall, the application of the forwardly moving pressure allows for delivery of the contained material. In this variation, it is preferable that the selectively breakable wall be broken only by either or both of the deformation of the tip (if tip 62 deformation is desired) and/or the application of the forwardly applied external pressure application means, so as to have a greater assurance that the material contained in the cartridge is actually delivered to the intended site regardless of the orientation in which the cartridge is held once the cap is removed. Selectively breakable container walls for the material to be contained within the cartridge can be made by having the desired wall be of substantially thinner construction than other walls or constructed of a substance that is inherently weaker than the other walls. Alternatively the selectively breakable container wall can be one that is perforated by or perforations of substantially smaller than the size which will allow flow of the materials contained therein without actual breakage of the wall. Other alternative container wall weakening methods will be apparent to those of ordinary skill in the art having access to the present disclosure.

The instantly claimed cartridge can be modified (without departing form the claimed invention) so as to fit in a working relationship with any pressure applying mechanism known in the art in order to deliver a forward moving pressure gradient which can be used to drive delivery of the material from the cartridge to the delivery site. One such non-limiting example of an external force applying member is that disclosed in U.S. Pat. No. 6,682,348.

The cartridge (without the material for delivery to be contained therein and without consideration of the internal plunger 100) which is attachable to an external pressure delivery source (hereinafter the "cartridge housing") is, in one preferred embodiment, generally made of a unitary construction from a moldable plastic material as may be known in the art and is generally rigid with certain degrees of flexibility imparted to specified regions such as the specified "corrugated region" (due to the "corrugated nature" of such region) and/or deformable tip region (due to it thinner cross-sectional dimension at the tip than at other regions and optional rigidity in other regions (such as in the portions which form the portions of the cartridge used to attach itself to and lock onto the external pressure applying means, primarily due to their greater thickness (relative to the tip portion)). When desired, the cartridge housing may be made in whole or in part of metal, provided the corrugated portion is present and the that region can be bent or extended as discussed elsewhere herein. In preferred embodiments which have the above discussed rigid ring 70 and the vertical rods 69 present, the multiple members 68 are firmly held in place relative to one another. In other embodiments, where the connectors 75, multiple rods 69, and/or the ring 70 are not part of the cartridge and not used in it, the multiple members 68 have greater degrees of freedom and may or may not be somewhat flexible (depending on the material from which they are constructed and thickness). In an alternate embodiment, the cartridge housing need not be of unitary construction, but can be made of separate portions that are assembled together. While the unitary construction offers the advantage of simplified construction, the non-unitary construction allows for use of different materials for the portions that need to be deformable and/or flexible from the materials used for portions that need to be more rigid. The greater rigidity of the ring 70 allows for easier handling and/or manipulation of the cartridge by the user.

In yet another embodiment (see FIG. 10), the multiple members 68, the ring 70 and the vertical rods 69 can all be dispensed with, and in this case, hollow tubular portion 50A is extended as needed to have sufficient length to appropriately engage with and lock onto the external pressure applying means.

The internal plunger 100 is preferably made from flexible material, including silicon rubber, pvc, polystyrene, or other similar material, metal may also be used if desired as long as the plunder is sufficiently flexible to navigate the range of bends that the corrugated portion can be bent into provided the plunger is also non-collapsible.

Turning from the device of the invention to the types of medicaments that can be administered from the invention device, virtually any medicament that can be administered in a form that suitably releases the active medicinal agent in the environment of use can be used in the present invention. As in most cases of applying the medicament to a body cavity such as in the pockets, crevices, and cracks in the oral cavity, there is more than sufficient moisture so that solid micro particles can readily dissolve. Similarly in many other body cavities, such as in the sinus cavity, vaginal cavity, uterus, bladder, and other internal organs mentioned above (inclusive of those cavities accessed via surgery (such as without limitation, the spinal column, the brain, the gall bladder, etc.)), there is also sufficient moisture present for the appropriate dissolution of the formulation and release of the medicament to the desired site of action. In other cavities, such as in the navel, the margins of the fingernail, the margins of the toenails, the ear canal, etc., there may not be sufficient moisture present for the suitable use of a dry micro particle and either a semisolid or semifluid dosage form is needed. These distinctions will be apparent to those of ordinary skill in the art and appropriate alterations in the formulations used will be readily understood by those of ordinary skill.

Turning to the medicinal uses for the present invention, these are limited only by the scope of medicinal agents that can be employed in the present invention and the location to which the agent needs to be deposited. One particularly useful area for utilization of the present invention is in the treatment of periodontal disease with antibiotics and other medicinal agents by direct application of these agents in the periodontal pockets. Another highly useful area is the treatment of sinus conditions by application of antibiotics, anti-inflammatories, and other desirable agents directly in the sinus cavity. Yet another highly useful application of the present invention is in the treatment of cancers (either operable or inoperable (such as in the brain or spine or around critical arteries) or substantial organ involvement prevents complete surgical removal. In such instances, application of anticancer agents directly into an inoperable mass allows for direct treatment with materials that may not be able to be delivered in any other manner at dosages which will be able to be effective. Pockets or cavities may naturally exist within such masses or may be made surgically into which the appropriate medication may be deposited by the use of the instant invention device. Many others will be apparent to those of ordinary skill in the art.

Thus, also within the invention is a method of maintaining health of the tissue to which the material is applied or treating a condition of a tissue to which the material is applied by administering the material to a patient via the use of the instant invention cartridge. The method comprises treating a tissue of the cavity in question by providing a cartridge of the present invention having contained therein a suitable material for the treatment of said tissue of the cavity, placing said cartridge tip into the cavity opening and dispensing the material into the cavity in question. In one preferable (but non-limiting) embodiment, the cavity in question is a gingival (or periodontal) pocket, typically associated with periodontal disease. Generally, the party administering the material activates an external force applying member which applies force to the plunger or alternative force translating means as previously discussed, which forces the material out of the tip and into the cavity or pocket in question. In some embodiments, the tip is deformed from its original cross-sectional geometry to a second cross-sectional geometry (generally more flattened or more oval than its original geometry) in the course of administering the material. When such tip deformation is accomplished by (without limitation) it is generally done by applying the tip against a tissue or wall of the cavity in question. Other manners of tip deformation may be used if desired and such other tip deformation operations would be known to those of ordinary skill in the art. In the case of the periodontal or gingival cavity, a non-limiting means of tip deformation may be accomplished by pressing the tip against a tooth surface or gum surface in the vicinity of the periodontal pocket and then placing the tip into the cavity opening or by placing the tip into the cavity opening and apply pressure so the tip is pressed against a surface internal to the cavity. However, as previously described, the deformation of the tip by applying pressure against the tissues or wall of the cavity opening or internal cavity surface is generally not desired due to the compromised or diseased nature of those tissues or surfaces.

In an analogous fashion, the present invention is further directed to methods of administering (as well as methods of treating conditions) of the various other tissues heretofore mentioned via administration of the material in question to a cavity, pocket, or crevice where such tissue is in need of having the material administered thereto locally, via dispensing the material from the cartridge of the present invention. The invention is also applicable in analogous fashion to animals in general, including human being, pets, farm animals, and wild animals. While the invention is of particular value to administration of substances to mammals, it is not so limited and can be used to apply suitable substances to non-mammals as well.

The present invention also has numerous applications outside of medical/veterinary field. These include any area of endeavor where material needs to be deposited in (a) spaces in cavities which are difficult to reach, primarily because the opening size is generally small and the desired deposition site is not otherwise accessible from the outside of the cavity; and (b) deposition sites that even though not true internal cavity spaces, are spaces that are encumbered by surrounding features which make access to the deposition site difficult. Such applications include, without limitation: (a) pesticide, herbicide, fungicide application in agrochemical areas; (b) pesticide application in pest control in the home and business settings (such as in cracks and crevices in wall joints or wall/floor abutments or into small openings into interior wall hollows; (c) application of sealants (such as, without limitation, glues, epoxies, etc.) in construction and repair of buildings; (d) application of glues in craft applications generally; (d) application of grout into ceramic tiling spaces; (e) application of sealants, cleaning agents, masks and photoresist layers in electronic manufacture; etc. One particularly useful area is the introduction of plaster where the surface that is accessible is small, but there is a substantial opening or cavity behind the opening. If one does not wish to enlarge the opening, getting sufficient plaster into the opening to have a substantial bond formed is often difficult, if not impossible. Using the cartridge of the present invention with a plaster paste (instead of the dry micro particles of the primary medicament embodiment discussed above), allows for one to introduce a significant amount of plaster behind the opening and filling the opening so that the exposed surface of the plaster in the opening has a much greater potential for being retained in the opening and keeping it sealed. The same can be said respect to application of caulking. Many other applications will be apparent to those of ordinary skill in the art without departing from the spirit of the invention.

Suitable active agents include all varieties provided their dosage amounts can be delivered to the site of action in a dosage form from which the active agent can be suitable released, such as, without limitation, antibacterials, antibiotics, anti-inflammatories, immunosuppressive agents, immuno-stimulatory agents, dental desensitizers, odor masking agents, immune reagents, anesthetics, antiseptics, nutritional agents, antioxidants, lipopolysaccharide complexing agents, a peroxide or peroxide precursor, a bone growth stimulant, a fluoridating agent, a hormone, a tissue growth factor, an anticancer agent, etc. and mixtures or combinations thereof. Each of these may be in the form of any or a mixture of salts, esters, hydrates, solvates, enantiomers, racemates, or polymorphs of the parent named compound. Those of ordinary skill would be well aware of specific agents within each of these classes as well as others. Particularly useful are antibiotics of all types, especially tetracyclines, more particularly doxycycline and minocycline. Formulations of the active agent can be solid, semi-solid, gel, a thick liquid, and liquid formulations of varying viscosities. A particularly suitable (non-limiting) formulation are those set out in U.S. Pat. No. 6,682,348 (incorporated herein in its entirety by reference). The '348 Patent incorporates U.S. Pat. Nos. 5,000,886, 5,143,661, 5,236,355, 5,366,733, 5,500,228, and 5,622,498, with respect to the suitable formulations, and these are also incorporated by reference in their entirety herein with respect to suitable (but non-limiting) formulations for use in the present cartridge dispensers. These compositions can be dispersed in matrices of biocompatible and biodegradable polymers, in accordance with the disclosures of the 7 patents mentioned in this paragraph. Such formulations of these 7 patents have the active agent dispersed in a biocompatible and biodegradable polymer. As stated, the material for dispensing from the invention cartridge is not limited to the formulations above, but is more generally applicable to a broad range of formulations. Non-limiting polymers in the polymers in the '348 Patent include for example, polyglycolide, poly(l-lactide), poly(dl) lactide, poly (glycolide-co-lactide) poly (glycolide-co-dl lactide), poly (alpha hydroxybutyric acid, poly(orthoesters), poly (p-dioxanone) and mixtures thereof. The polymers can also be block copolymers of polyglycolide, trimethylene carbonate and polyethylene oxide.

Without limitation, a suitable formulation comprises dry microparticles comprising the active agent in an amount of about 0.01 to about 75 parts by weight per 100 parts by weight of the dry microparticles, preferably about 10 to about 70 parts by weight per 100 parts by weight of the dry microparticles. The dry microparticles typically have a diameter of about 0.1 to about 1000 microns, preferably about 20 to about 120 microns.

The instant disclosure provides preferred embodiments of a cartridge, the description of the cartridge, components thereof and methods of use thereof, all of which are exemplary only. Those skilled in the art will recognize, or be able to ascertain using routine experimentation, many equivalents to the specific embodiments of the invention described herein. Such equivalents are intended to be encompassed by the following claims.

The invention claimed is:

1. A cartridge device comprising: (a) a rigid body portion, said body portion having a first side, and an opposite side distal to said first side, (b) at least one temporary locking engagement capable portion extending from said first side of said body portion, said at least one temporary locking engagement capable portion being capable of engaging with an external-force-applying-member to form said temporary locking, engagement and having sufficient flexibility to enter into a temporary locking engagement and to be disengaged therefrom; and (c) a tube portion wherein: the tube portion having an external wall and an internal wall, said internal wall defining a tube portion internal diameter, said tube portion extending from the opposite side of said body portion; wherein the tube portion comprises a means-for-translating-a-farce, said means-for-translating-a-force contained partially within said body portion and partially within said tube portion, a corrugated portion located between a distal tip and the body portion, said distal tip having an exit opening, said means-for-translating-a-force capable of transmitting a force from said external-force-applying-member to at least one therapeutic agent material located within said distal tip and intended to be dispensed from said cartridge to a mammalian body surface or into a mammalian body cavity via said exit opening in the distal tip wherein said exit opening has an initial geometry and is not deformable to a geometry different from said initial geometry; said means-for-translating-a-force extending from said body portion into said tube portion and past aid corrugated portion of said tube portion to end at a position that is further removed from said body portion than said corrupted portion is from said body portion; said corrugated portion being on the external wall of said tube portion and extending partially through said wall of said tube portion toward said internal wall of said tube portion but not extending completely to the internal wall of said tube portion so that the external wall has radially outward peaks and radially inward valleys defining said corrugations and said internal wall not having any radially outward or radially inward peaks and valleys, said internal wall of said tube portion being smooth and/or tapering, said tapering being from a larger diameter to a smaller diameter, which said larger diameter is located at a position closer to mid body portion than said smaller diameter and said smaller diameter is located closer to said tip portion than said larger diameter such that said tapering-extends across said corrugated portion region of said tube portion said corrugated portion permitting one or more bends to be introduced into the tube portion in said corrugated portion, either during initial manufacture or by a user prior to actual use of said device: and said tube portion, other than flexibility provided by said corrugated portion, being rigid.

2. The cartridge of claim 1, further comprising at least one elevated ridge along at least a section of the body portion wherein at least one of said at last one elevated ridge slidably engages with a channel portion within the external-force-applying-member to further aid in forming said temporary locking engagement.

3. The cartridge of claim 2
wherein
the distal tip further comprising an internal elevated portion.

4. The cartridge of claim 1 wherein the body portion includes more than one of said at least one member capable of the temporary locking engagement with at least a portion of said external-force-applying-member.

5. The cartridge of claim 1 wherein the tube portion comprises a quantity of dry particles, the dry articles being located within the distal tip.

6. The cartridge of claim 1 wherein, the external-force-applying-member is a syringe with a movable shaft.

7. The cartridge of claim 1 wherein, the distal tip comprises an internal elevated portion.

8. The cartridge of claim 1 wherein the location within the mammalian body is a periodontal pocket, a nasal cavity, a sinus cavity, an ear canal, brain, urethra, rectum, vaginal cavity, uterus, a tissue surrounding a finger nail or toe nail, a surgically created cavity, or a cavity resulting from a disease condition or process.

9. The cartridge of claim 1, wherein portions between said corrugated portion and said distal tip defining a finger portion and portions between said corrugated portion and said body portion defining a neck portion, and wherein the corrugated portion within the tube portion facilitates fie movement of the finger portion succeeding the corrugated portion so as to enable the distal tip to be moved from one spatial position to at least one other spatial position, and thereby affording different angles selected from the group consisting of angles in the range of from about 180 degrees to about 5 degrees between said finger portion and the neck portion and further allowing for counter angling.

10. The cartridge of claim 1, wherein the material is selected from dry particles, a semi-solid substance, gel, a liquid, a thick liquid, or a combination thereof.

11. The cartridge of claim 10, wherein the dry particles comprise at least one of said at least one therapeutic agent.

12. The cartridge of claim 11, wherein the dry particles comprise an effective amount of the at lea one therapeutic agent, the therapeutic agent dispersed in a dry matrix comprising a biocompatible and biodegradable polymer.

13. The cartridge of claim 12, wherein the therapeutic agent is selected from the group consisting of an antibacterial, an antibiotic, an anti-inflammatory agent, an immunosuppressive agent, an immunostimulatory agent, a dentinal desensitizer, an odor masking agent, an immune reagent, an anesthetic, an antiseptic, a nutritional agent, an antioxidant, a lipopolysaccharide complexing agent, a peroxide, a bone growth stimulant, a fluoridating agent, a hormone, a tissue growth factor and mixtures thereof.

14. The cartridge of claim 13, wherein the therapeutic agent has antibiotic activity.

15. The cartridge of claim 14, wherein the therapeutic agent comprises an antibiotic selected from the group consisting of a tetracycline, a pharmaceutically acceptable salt of a tetracycline, hydrates of a tetracycline and hydrates of a pharmaceutically acceptable salt of a tetracycline.

16. The cartridge of claim 15, wherein the therapeutic agent comprises a tetracycline selected from the group consisting of doxycycline, a pharmaceutically acceptable salt of doxycycline, hydrates of doxycycline and hydrates of a pharmaceutically acceptable salt of doxycycline.

17. The cartridge of claim 16, wherein the therapeutic agent comprises from about 0.01 to about 75 parts by weight per 100 parts by weight of the particles.

18. The cartridge of claim 17, wherein the therapeutic agent comprises from about 10 to about 70 parts by weight per 100 pars by weight of the particles.

19. The cartridge of claim 16, wherein the particles have a diameter of from about 0.1 to about 1000 microns.

20. The cartridge of claim 19, wherein the particles have a diameter of from about 20 to about 120 microns.

21. The cartridge of claim 15, wherein the therapeutic agent comprises a tetracycline selected from the group consisting of minocycline, a pharmaceutically acceptable salt of minocycline, hydrates of minocycline and hydrates of a pharmaceutically acceptable salt of minocycline.

22. The cartridge of claim 21, wherein the therapeutic agent comprises from about 0.01 to about 75 parts by weight per 100 parts by weight of the particles.

23. The cartridge of claim 22, wherein the therapeutic agent comprises from about 10 to about 70 parts by weight per 100 parts by weight of the particles.

24. The cartridge of claim 21, wherein the particles have a diameter of from about 0.1 to about 1000 microns.

25. The cartridge of claim 24, wherein the particles have a diameter of from about 20 to about 120 microns.

26. A cartridge device comprising (a) a rigid body portion, said body portion having a first side, and an opposite side distal to said first side, (b) at least one temporary locking engagement capable portion extending from said first side of said body portion, said at least one temporary locking engagement capable portion being capable of engaging with an extremal-force-applying-member to form a temporary locking engagement and having sufficient flexibility to enter into maid temporary locking engagement and to be disengaged therefrom; and (c) a tube portion wherein: the tube portion having an external wall and an internal wall, said internal wall defining a tube portion internal diameter, said tube portion extending from the opposite side of said body portion; wherein the tube portion comprises a plunger, said plunger contained partially within said body portion and partially within said tube portion, a corrugated portion located between a distal tip and the body portion, said plunger capable of transmitting a force from said external-force-applying-member to at least one therapeutic agent material located within said distal tip and intended to be dispensed form said cartridge to a mammalian body surface or into a mammalian body cavity via an exit opening in the distal tip wherein said exit opening has an initial geometry and is not deformable to a geometry different from said initial geometry; said plunger extending from said body poi into said tube portion and past said corrugated portion of said tube portion to end at a position that is further removed from maid body portion than said corrugated portion is from said body portion; said corrugated portion being on the external wall of said tube portion and extending partially through said wall of said tube portion toward said internal wall of said tube portion but not extending completely to the internal wall of said tube portion so that the external wall has radially outward peaks and radially inward valleys defining aid corrugations and said internal wall not having any radially outward or radially inward peaks and valleys, said internal wall of said tube portion being smooth and/or tapering, said tapering being from a larger diameter to smaller diameter, which said larger diameter is located at a position closer to said body portion than said smaller diameter and said smaller diameter is located closer to said tip portion than said larger diameter such that said tapering extends across said corrugated portion resion of said tube portion, said corrugation portion permitting one or more bends to be introduced into the tube portion in said corrugated portion, either during initial manufacture or by a user prior to actual use of said device; and said tube portion, other than flexibility provided by said corrugated portion, being rigid.

\* \* \* \* \*